US00PP09690P

United States Patent [19]

VandenBerg

[11] Patent Number: Plant 9,690

[45] Date of Patent: Nov. 12, 1996

[54] CHRYSANTHEMUM PLANT NAMED 'MADERA'

[75] Inventor: Cornelis P. VandenBerg, Salinas, Calif.

[73] Assignee: Yoder Brothers, Inc., Barberton, Ohio

[21] Appl. No.: 547,325

[22] Filed: Oct. 24, 1995

[51] Int. Cl.[6] ..... A01H 5/00

[52] U.S. Cl. ..... Plt./79

[58] Field of Search ..... Plt./76, 78, 79

*Primary Examiner*—Howard J. Locker

*Attorney, Agent, or Firm*—Foley & Lardner

[57] ABSTRACT

A Chrysanthemum plant named Madera particularly characterized by its flat capitulum form; decorative capitulum type; yellow-orange ray floret color with a darker center of the flower in the orange group; diameter across face of capitulum of 79 to 86 mm when fully opened, when grown as a single stem spray cut mum; flowering response in Salinas under normal temperatures is 58 to 64 days after start of short days; flowering response in Bogota, Colombia is 68 to 76 days; plant height is 89 to 107 cm when grown in Salinas with 11 long days prior to start of short days; plant height is 99 to 109 cm when grown in Bogota with 14 to 15 long days prior to start of short days; peduncle length of the first lateral at flowering after removing the apical bud is 8 to 10 cm when grown in Salinas, and 10 to 15 cm when grown in Bogota; peduncle length of the fourth lateral at flowering is 10 to 15 cm when grown in Salinas, and 15 to 18 cm when grown in Bogota; excellent tolerance to low night temperatures for bud initiation and flower development; and recommended as a spray cut mum.

3 Drawing Sheets

The present invention comprises a new and distinct cultivar of Chrysanthemum, botanically known as *Dendranthema grandiflora,* and referred to by the cultivar name Madera.

Madera, identified as 1421 (90-035004), was originated from a cross made by Cornelis P. VandenBerg in a controlled breeding program in Salinas, Calif., in 1989.

The female parent of Madera was the cultivar identified as Pasion, disclosed in U.S. Plant Pat. No. 7,489, and described as a light red-purple spray cut mum, with a darker center of the flower.

The male parent of Madera was an unnamed seedling, identified as 1359 (85-271002) and described as white decorative spray cut mum with many disc florets.

Madera was discovered and selected as one flowering plant within the progeny of the stated cross by Cornelis P. VandenBerg in April 1991, in a controlled environment in Salinas, Calif.

The first act of asexual reproduction of Madera was accomplished when vegetative cuttings were taken from the initial selection in June 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Madera are firmly fixed and are retained through successive generations of asexual reproduction.

Madera has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia, with an average minimum low night temperature inside the greenhouse during our trials ranging as low as 5 to 8 degrees Celsius.

The following traits have been repeatedly observed and are determined to be basic characteristics of Madera, which, in combination, distinguish this Chrysanthemum as a new and distinct cultivar.

1. Flat capitulum form.
2. Decorative capitulum type.
3. Yellow-orange ray floret color with a darker center of the flower in the orange group.
4. Diameter across face of capitulum of 79 to 86 mm when fully opened, when grown as a single stem spray cut mum.
5. Flowering response in Salinas under normal temperatures is 58 to 64 days after start of short days. Flowering response in Bogota, Colombia is 68 to 76 days.
6. Plant height is 89 to 107 cm when grown in Salinas with 11 long days prior to start of short days; plant height is 99 to 109 cm when grown in Bogota with 14 to 15 long days prior to start of short days.
7. Peduncle length of the first lateral at flowering after removing the apical bud is 8 to 10 cm when grown in Salinas, and 10 to 15 cm when grown in Bogota. Peduncle length of the fourth lateral at flowering is 10 to 15 cm when grown in Salinas, and 15 to 18 cm when grown in Bogota.
8. Excellent tolerance to low night temperatures for bud initiation and flower development.
9. Recommended as a spray cut mum.

The accompanying photographic drawings show typical inflorescence and leaf characteristics of Madera, with the colors being as nearly true as possible with illustrations of this type.

Sheet 1 is a color photograph of Madera grown as a single stem spray cut mum, grown in Salinas, Calif.

Sheet 2 is a black and white photograph of three views of the inflorescence of Madera.

Sheet 3 is a black and white photograph showing the upper and under sides of the leaves of Madera at 3 stages of development (mature, intermediate and immature). In sheets 2 and 3 a measuring tape in centimeters has been added.

Of the commercial cultivars known to the inventor, the most similar in comparison to Madera is the cultivar identified as Falma, disclosed in U.S. Plant Pat. No. 5,996. Reference is made to attached Chart A, which compares certain characteristics of Madera with the same characteristics of Falma. Similar traits are capitulum form and type. The ray floret color of both Madera and Falma is described as yellow-orange. However, the ray floret color of Madera is significantly lighter than the ray floret color of Falma, while Madera has a distinct darker center of the flower in the orange group. Falma does not have a darker center of the flower. Madera has a larger diameter of capitulum, a slower flowering response to short days, a shorter plant height and shorter peduncles when compared with Falma.

In the following description color references are made to The Royal Horticultural Society Colour Chart. The color values were determined on plant material grown as a single stem spray cut mum in Salinas, Calif. on Jun. 20, 1994.

Classification:

*Botanical.*—*Dendranthema grandiflora* cv Madera

*Commercial.*—Flat decorative spray cut mum.

INFLORESCENCE

A. Capitulum:

*Form.*—Flat.

*Type.*—Decorative.

*Diameter across face.*—79 to 86 mm when fully opened.

B. Corolla of ray florets:

*Color (general tonality from a distance of three meters).*—Yellow-orange with darker centers of the flower in the orange group.

*Color (upper surface).*—17B to 17C, center of flower 26A to 26B.

*Color (under surface).*—17C.

*Shape.*—Straight, cross section concave, pointed petal tip.

C. Corolla of disc florets:

*Color (mature).*—Closest to 15A.

*Color (immature).*—Closest to 144B.

D. Reproductive organs:

*Androecium.*—Present on disc florets only; no pollen.

*Gynoecium.*—Present on both ray and disc florets.

PLANT

A. General appearance:

*Height.*—89 to 107 cm when grown in Salinas with 11 long days prior to start of short days; 99 to 109 cm when grown in Bogota with 14 to 15 long days prior to start of short days.

B. Foliage:

*Color (upper surface).*—147A.

*Color (under surface).*—147B.

*Shape.*—Deeply lobed, serrated.

CHART A
COMPARISON OF MADERA AND FALMA

| CHARACTERISTIC | MADERA | FALMA |
|---|---|---|
| Ray floret color | Yellow-orange | Yellow-orange |
| Capitulum form | Flat | Flat |
| Capitulum type | Decorative | Decorative |
| Diameter across face of capitulum | 79 to 86 mm | 57 to 64 mm |
| Flowering response | | |
| in Salinas | 58 to 64 days | 49 to 56 days |
| in Bogota | 68 to 76 days | 63 to 68 days |
| Plant height with | | |
| 6–11 long days Salinas | 81 to 97 cm | 91 to 102 cm |
| 14–15 long days Bogota | 99 to 109 cm | 109 to 119 cm |
| Peduncle length | | |
| 1st lateral, Salinas | 8 to 10 cm | 10 to 13 cm |
| 4th lateral Salinas | 10 to 15 cm | 15 to 18 cm |
| 1st lateral, Bogota | 10 to 15 cm | 13 cm |
| 4th lateral, Bogota | 15 to 18 cm | 18 to 20 cm |

COMPARISONS MADE OF PLANTS GROWN AS SINGLE STEM SPRAY CUT MUM IN SALINAS, CALIFORNIA AND IN BOGOTA, COLOMBIA

What is claimed is:

1. A new and distinct Chrysanthemum plant named Madera, as described and illustrated.

* * * * *

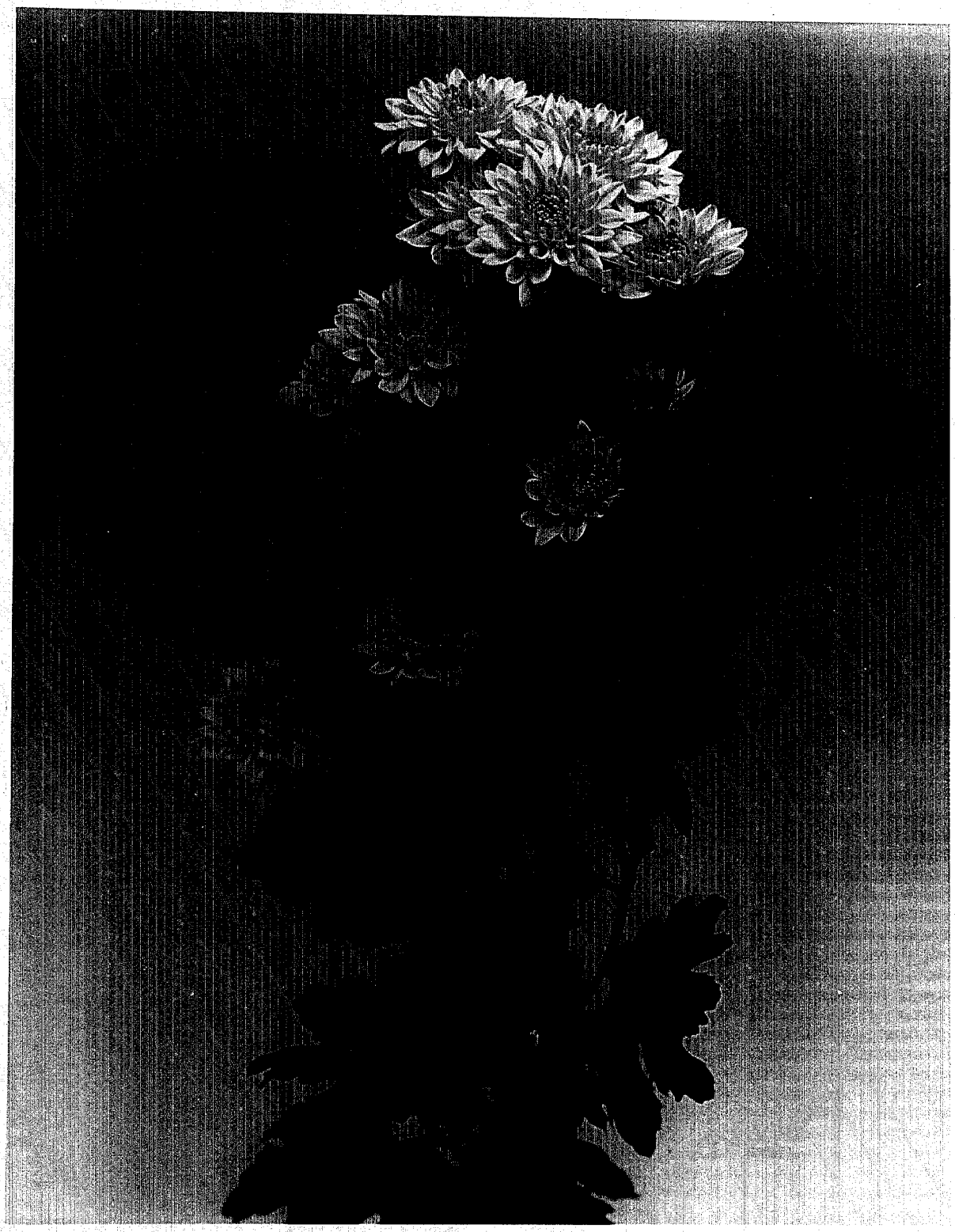

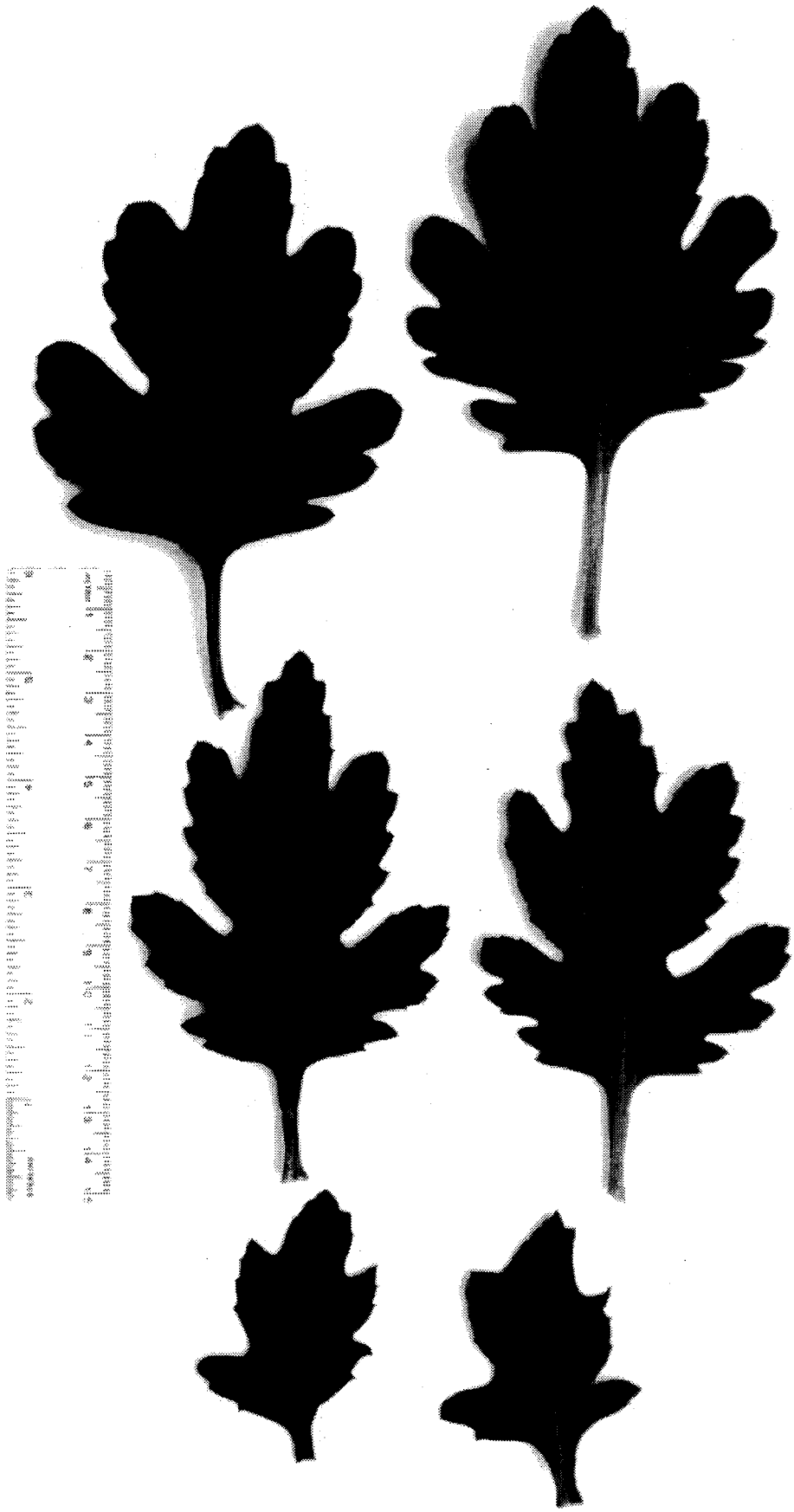

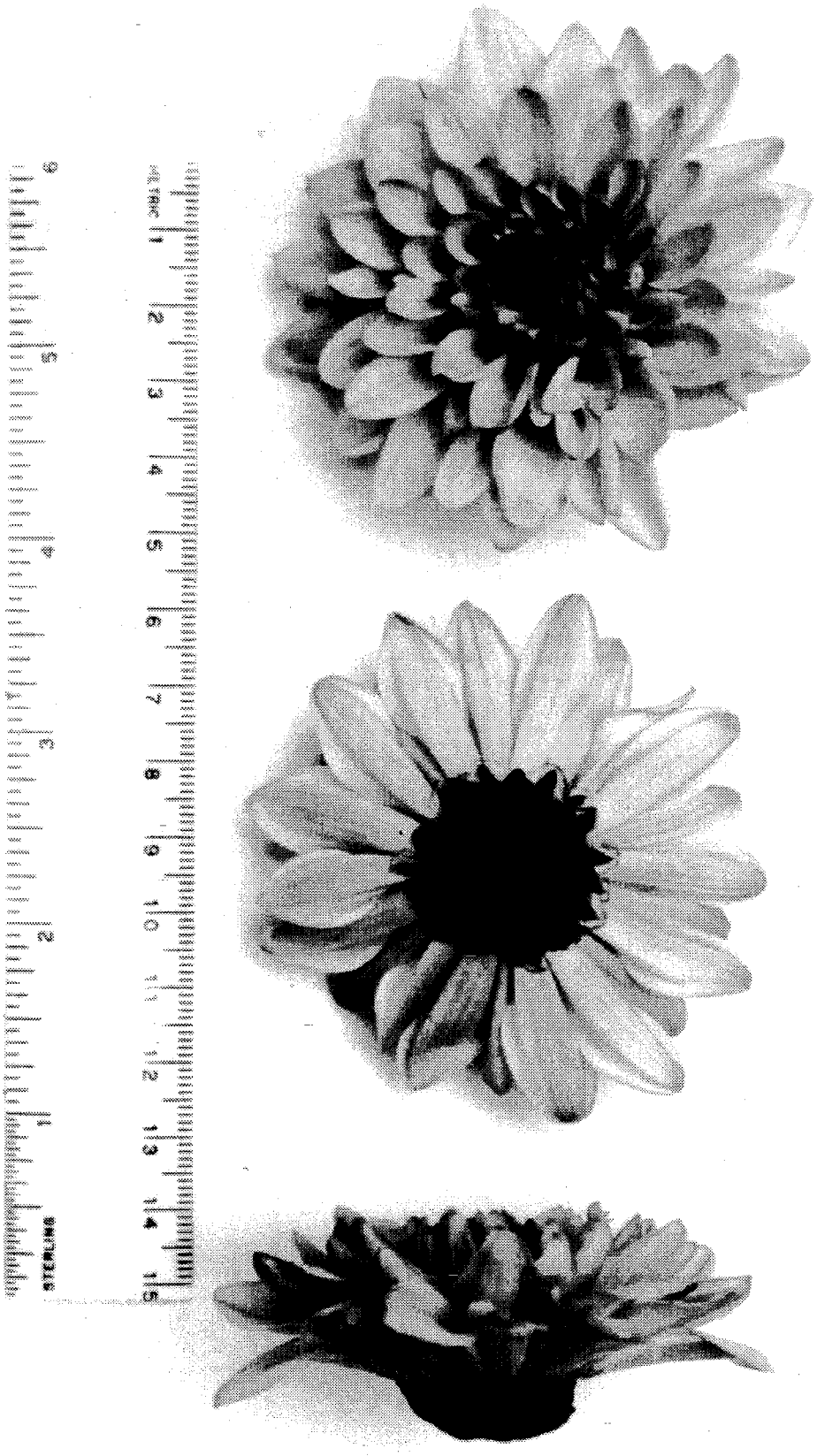
STERLING